US 9,592,359 B2

(12) United States Patent
Kwok et al.

(10) Patent No.: US 9,592,359 B2
(45) Date of Patent: *Mar. 14, 2017

(54) FOREHEAD SUPPORT FOR FACIAL MASK (75) Inventors: Philip R. Kwok, Chatswood (AU);
Michael K. Gunaratnam, Marsfield (AU); Perry D. Lithgow, Moruya (AU); Jonathan P. Harrison, Ponsonby (NZ); Jonathan L. Liston, Coogee (AU); Robert S. Matchett, Mosman (AU); Robert E. Styles, Glenhaven (AU)

(73) Assignee: ResMed Limited, Bella Vista (AU)

( * ) Notice: Subject to any disclaimer, the term of this patent is extended or adjusted under 35 U.S.C. 154(b) by 812 days.

This patent is subject to a terminal disclaimer.

(21) Appl. No.: 13/470,962

(22) Filed: May 14, 2012

(65) Prior Publication Data
US 2012/0222681 A1 Sep. 6, 2012

Related U.S. Application Data (60) Continuation of application No. 12/585,732, filed on Sep. 23, 2009, now Pat. No. 8,186,348, which is a
(Continued)

(30) Foreign Application Priority Data

Jun. 18, 1999 (AU) ..................................... PQ 1040

(51) Int. Cl.
*A61M 16/06* (2006.01)
*A61M 16/08* (2006.01)

(52) U.S. Cl.
CPC ........ *A61M 16/0683* (2013.01); *A61M 16/06* (2013.01); *A61M 16/0605* (2014.02);
(Continued)

(58) Field of Classification Search
CPC .............. A61M 16/06; A61M 16/0633; A61M 16/0638; A61M 16/0644; A61M 16/065;
(Continued)

(56) References Cited

U.S. PATENT DOCUMENTS 781,516 A 1/1905 Guthrie
812,706 A 2/1906 Warbasse
(Continued)

FOREIGN PATENT DOCUMENTS

AU 91/77110 B 11/1991
AU 94/64816 B 12/1994
(Continued)

OTHER PUBLICATIONS

Kwok et al, Australian PQ 1040, Jun. 18, 1999.*
(Continued)

*Primary Examiner* — Victoria J Hicks
*Assistant Examiner* — Camtu Nguyen
(74) *Attorney, Agent, or Firm* — Nixon & Vanderhye P.C.

(57) ABSTRACT

A respiratory mask assembly includes a respiratory mask including a mask shell and a mask cushion, a forehead support adjustably coupled to the mask, and an angular adjustment member. The forehead support includes a joining member provided to the mask shell and a cushion frame pivotally mounted to the joining member. The cushion frame is adapted to be selectively locked against pivotal movement in at least three predetermined angular positions relative to the joining member by a tongue and slot arrangement. The angular adjustment member allows relative angular adjustment between the cushion frame and the joining member. The angular adjustment member includes a pair of flexible arms that are adapted to be flexed towards one another to disengage the tongue from a respective one of the slots, and releasing the flexible arms allows the flexible arms to
(Continued)

resiliently flex away from one another to engage the tongue and the respective slot.

30 Claims, 8 Drawing Sheets

Related U.S. Application Data division of application No. 11/510,607, filed on Aug. 28, 2006, now Pat. No. 7,610,916, which is a continuation of application No. 10/700,252, filed on Nov. 4, 2003, now Pat. No. 7,234,466, which is a continuation of application No. 10/264,326, filed on Oct. 4, 2002, now Pat. No. 6,860,269, which is a continuation of application No. 09/502,745, filed on Feb. 11, 2000, now Pat. No. 6,532,961.

(52) U.S. Cl.
CPC .... *A61M 16/0616* (2014.02); *A61M 16/0622* (2014.02); *A61M 16/0633* (2014.02); *A61M 16/0638* (2014.02); *A61M 16/0666* (2013.01); *A61M 16/08* (2013.01); *A61M 16/0816* (2013.01); *A61M 2205/02* (2013.01); *A61M 2210/0618* (2013.01); *Y10T 24/45529* (2015.01)

(58) Field of Classification Search
CPC .......... A61M 16/0655; A61M 16/0683; A61M 25/02; A61M 16/0605; A61M 16/0661; A61M 16/0666; A61M 16/0672; A61M 16/0677; A61M 16/0688; A61M 16/0694; A62B 18/08; A62B 18/00; A62B 18/02; A62B 18/04; A62B 18/06; A61F 2025/0213; A61B 18/084; A42B 3/22; A42B 3/225
USPC ............ 128/206.24, 206.21, 206.27, 206.28, 128/207.11, 206.12, 206.13, 205.25, 128/203.29, 201.23, 201.24
See application file for complete search history.

(56) References Cited

U.S. PATENT DOCUMENTS

| | | | |
|---|---|---|---|
| 1,075,693 A | 10/1913 | Cassidy | |
| 1,081,745 A | 12/1913 | Johnston et al. | |
| 1,653,572 A | 12/1927 | Jackson | |
| 1,926,027 A | 9/1933 | Biggs | |
| 2,123,353 A | 7/1938 | Catt | |
| 2,245,658 A * | 6/1941 | Erickson | 128/206.28 |
| 2,245,969 A | 6/1941 | Francisco et al. | |
| 2,248,477 A | 7/1941 | Lombard | |
| 2,254,854 A | 9/1941 | O'Connell | |
| 2,317,606 A | 4/1943 | Heidbrink | |
| 2,371,965 A | 3/1945 | Lehmberg | |
| 2,376,671 A | 5/1945 | Fink | |
| 2,398,269 A * | 4/1946 | Young | 2/8.1 |
| 2,415,846 A | 2/1947 | Randall | |
| 2,438,058 A | 3/1948 | Kincheloe | |
| 2,488,898 A | 11/1949 | Brasty | |
| 2,578,621 A | 12/1951 | Yant | |
| 2,590,006 A | 3/1952 | Gordon | |
| 2,874,693 A * | 2/1959 | Matheson | 128/206.15 |
| 2,931,356 A | 4/1960 | Schwarz | |
| D188,084 S | 5/1960 | Garelick | |
| 2,939,458 A | 6/1960 | Lundquist | |
| 3,013,556 A | 12/1961 | Galleher | |
| 3,182,659 A | 5/1965 | Blount et al. | |
| 3,189,027 A | 6/1965 | Bartlett | |
| 3,193,624 A | 7/1965 | Webb et al. | |
| 3,234,939 A * | 2/1966 | Morton, Jr. | 128/206.27 |
| 3,238,943 A | 3/1966 | Holley | |
| 3,315,674 A | 4/1967 | Bloom et al. | |
| 3,330,273 A | 7/1967 | Bennett | |
| 3,362,420 A | 1/1968 | Blackburn et al. | |
| 3,363,833 A | 1/1968 | Laerdal | |
| 3,556,122 A | 1/1971 | Laerdal | |
| 3,580,051 A | 5/1971 | Blevins | |
| 3,700,000 A | 10/1972 | Hesse et al. | |
| 3,720,235 A | 3/1973 | Schrock | |
| 3,750,333 A | 8/1973 | Vance | |
| 3,752,157 A | 8/1973 | Malmin | |
| 3,796,216 A | 3/1974 | Schwarz | |
| 3,799,164 A | 3/1974 | Rollins | |
| D231,803 S | 6/1974 | Huddy | |
| 3,830,230 A | 8/1974 | Chester | |
| 4,077,404 A | 3/1978 | Elam | |
| 4,098,270 A * | 7/1978 | Dolby | 128/206.12 |
| D250,131 S | 10/1978 | Lewis et al. | |
| 4,120,302 A | 10/1978 | Ziegler | |
| 4,167,185 A | 9/1979 | Lewis | |
| 4,226,234 A | 10/1980 | Gunderson | |
| 4,245,632 A | 1/1981 | Houston | |
| D262,322 S | 12/1981 | Mizerak | |
| 4,304,229 A | 12/1981 | Curtin | |
| 4,328,797 A | 5/1982 | Rollins et al. | |
| 4,347,205 A | 8/1982 | Stewart | |
| 4,354,488 A | 10/1982 | Bartos | |
| 4,402,316 A * | 9/1983 | Gadberry | 128/201.15 |
| 4,412,537 A | 11/1983 | Tiger | |
| 4,467,799 A | 8/1984 | Steinberg | |
| 4,522,639 A | 6/1985 | Ansite et al. | |
| 4,558,710 A | 12/1985 | Eichler | |
| 4,616,647 A | 10/1986 | McCreadie | |
| 4,622,964 A | 11/1986 | Flynn | |
| 4,655,213 A | 4/1987 | Rapoport et al. | |
| 4,665,570 A | 5/1987 | Davis | |
| 4,671,271 A | 6/1987 | Bishop et al. | |
| 4,677,975 A | 7/1987 | Edgar et al. | |
| 4,677,977 A | 7/1987 | Wilcox | |
| D293,613 S | 1/1988 | Wingler | |
| 4,739,755 A | 4/1988 | White et al. | |
| 4,770,169 A | 9/1988 | Schmoegner et al. | |
| 4,774,941 A | 10/1988 | Cook | |
| 4,782,832 A | 11/1988 | Trimble et al. | |
| 4,799,477 A | 1/1989 | Lewis | |
| 4,809,692 A | 3/1989 | Nowacki et al. | |
| 4,819,629 A | 4/1989 | Jonson | |
| 4,821,713 A | 4/1989 | Bauman | |
| 4,841,953 A | 6/1989 | Dodrill | |
| 4,848,334 A | 7/1989 | Bellm | |
| 4,848,366 A | 7/1989 | Aita et al. | |
| 4,907,584 A | 3/1990 | McGinnis | |
| 4,910,806 A | 3/1990 | Baker et al. | |
| 4,919,128 A | 4/1990 | Kopala et al. | |
| 4,938,210 A | 7/1990 | Shene | |
| 4,938,212 A | 7/1990 | Snook et al. | |
| 4,944,310 A | 7/1990 | Sullivan | |
| D310,431 S | 9/1990 | Bellm | |
| 4,971,051 A | 11/1990 | Toffolon | |
| 4,986,269 A | 1/1991 | Hakkinen | |
| 4,989,596 A | 2/1991 | Macris et al. | |
| 4,989,599 A | 2/1991 | Carter | |
| 5,005,568 A | 4/1991 | Loescher et al. | |
| 5,005,571 A | 4/1991 | Dietz | |
| 5,038,776 A | 8/1991 | Harrison et al. | |
| 5,042,473 A | 8/1991 | Lewis | |
| 5,042,478 A | 8/1991 | Kopala et al. | |
| 5,046,200 A | 9/1991 | Feder | |
| 5,063,922 A | 11/1991 | Hakkinen | |
| 5,069,205 A | 12/1991 | Urso | |
| D323,908 S | 2/1992 | Hollister et al. | |
| 5,109,839 A | 5/1992 | Blasdell et al. | |
| 5,109,840 A | 5/1992 | Daleiden | |
| 5,121,745 A | 6/1992 | Israel | |
| 5,133,347 A | 7/1992 | Huennebeck | |
| 5,140,980 A | 8/1992 | Haughey et al. | |
| 5,140,982 A | 8/1992 | Bauman | |
| 5,159,938 A | 11/1992 | Laughlin | |
| 5,178,138 A | 1/1993 | Walstrom et al. | |

(56) References Cited

U.S. PATENT DOCUMENTS

| | | | |
|---|---|---|---|
| 5,181,507 A * | 1/1993 | Michel et al. ............ 128/201.25 |
| D334,633 S | 4/1993 | Rudolph |
| 5,220,699 A | 6/1993 | Farris |
| 5,231,983 A | 8/1993 | Matson et al. |
| 5,233,978 A | 8/1993 | Callaway |
| 5,243,971 A * | 9/1993 | Sullivan et al. ......... 128/205.25 |
| 5,265,595 A | 11/1993 | Rudolph |
| 5,279,289 A | 1/1994 | Kirk |
| 5,280,784 A | 1/1994 | Kohler |
| 5,311,862 A | 5/1994 | Blasdell et al. |
| 5,322,057 A | 6/1994 | Raabe et al. |
| 5,322,059 A | 6/1994 | Walther |
| 5,343,878 A | 9/1994 | Scarberry et al. |
| 5,357,951 A | 10/1994 | Ratner |
| 5,372,130 A | 12/1994 | Stern et al. |
| 5,388,571 A | 2/1995 | Roberts et al. |
| 5,404,871 A | 4/1995 | Goodman et al. |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis et al. |
| 5,479,920 A | 1/1996 | Piper et al. |
| 5,481,763 A | 1/1996 | Brostrom et al. |
| 5,488,948 A | 2/1996 | Dubruille et al. |
| 5,492,116 A | 2/1996 | Scarberry et al. |
| 5,501,214 A | 3/1996 | Sabo |
| 5,509,404 A | 4/1996 | Lloyd et al. |
| 5,517,986 A | 5/1996 | Starr et al. |
| 5,538,000 A | 7/1996 | Rudolph |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,570,682 A | 11/1996 | Johnson |
| 5,570,689 A | 11/1996 | Starr et al. |
| 5,571,217 A | 11/1996 | Del Bon et al. |
| D377,089 S | 12/1996 | Starr et al. |
| 5,592,938 A | 1/1997 | Scarberry et al. |
| 5,608,647 A | 3/1997 | Rubsamen et al. |
| 5,642,730 A | 7/1997 | Baran |
| 5,647,355 A | 7/1997 | Starr et al. |
| 5,647,357 A | 7/1997 | Barnett et al. |
| 5,649,532 A | 7/1997 | Griffiths |
| 5,649,533 A | 7/1997 | Oren |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,662,101 A | 9/1997 | Ogden et al. |
| 5,666,946 A | 9/1997 | Langenback |
| 5,685,296 A | 11/1997 | Zdrojkowski et al. |
| 5,687,715 A | 11/1997 | Landis et al. |
| 5,715,814 A | 2/1998 | Ebers |
| 5,746,201 A | 5/1998 | Kidd |
| 5,813,423 A | 9/1998 | Kirchgeorg |
| 5,832,918 A | 11/1998 | Pantino |
| 5,944,564 A * | 8/1999 | Chadbourne ........ H01R 4/2404 439/783 |
| 6,016,804 A * | 1/2000 | Gleason et al. ............ 128/206.17 |
| 6,044,844 A | 4/2000 | Kwok et al. |
| 6,119,693 A * | 9/2000 | Kwok ................ A61M 16/06 128/201.11 |
| 6,192,886 B1 * | 2/2001 | Rudolph .............. A61M 16/06 128/205.25 |
| D439,326 S * | 3/2001 | Hecker ................... D24/110.1 |
| D443,355 S | 6/2001 | Gunaratnam et al. |
| 6,374,826 B1 | 4/2002 | Gunaratnam et al. |
| 6,412,487 B1 | 7/2002 | Gunaratnam et al. |
| 6,463,931 B1 | 10/2002 | Kwok et al. |
| 6,467,483 B1 | 10/2002 | Kopacko et al. |
| 6,520,182 B1 | 2/2003 | Gunaratnam |
| 6,532,961 B1 | 3/2003 | Kwok et al. |
| D484,238 S | 12/2003 | Radney et al. |
| 6,691,708 B2 | 2/2004 | Kwok et al. |
| D489,817 S | 5/2004 | Ankey et al. |
| 6,860,269 B2 | 3/2005 | Kwok et al. |
| 7,000,614 B2 | 2/2006 | Lang et al. |
| 7,047,971 B2 | 5/2006 | Ho et al. |
| 7,066,179 B2 | 6/2006 | Eaton et al. |
| 7,069,932 B2 | 7/2006 | Eaton et al. |
| 7,234,466 B2 * | 6/2007 | Kwok et al. ............. 128/207.11 |
| 7,610,916 B2 * | 11/2009 | Kwok et al. ............. 128/207.11 |
| 8,186,348 B2 * | 5/2012 | Kwok et al. ............. 128/207.11 |
| 1,192,186 A1 | 7/2016 | Greene |
| 2003/0019496 A1 | 1/2003 | Kopacko et al. |
| 2003/0221691 A1 | 12/2003 | Biener et al. |
| 2004/0045551 A1 | 3/2004 | Eaton et al. |
| 2004/0099272 A1 | 5/2004 | Kwok et al. |
| 2010/0012129 A1 | 1/2010 | Kwok et al. |

FOREIGN PATENT DOCUMENTS

| | | |
|---|---|---|
| AU | 95/16178 B | 7/1995 |
| AU | 9459430 | 2/1996 |
| AU | A 32914/95 | 2/1996 |
| AU | A 41018/97 | 4/1998 |
| AU | A 89312/98 | 1/1999 |
| CA | 1039144 | 9/1928 |
| CN | 1326371 A | 12/2001 |
| CN | 1408453 A | 4/2003 |
| DE | 459 104 | 4/1926 |
| DE | 701 690 | 1/1941 |
| DE | 923 500 | 2/1955 |
| DE | 159396 | 6/1981 |
| DE | 3015279 A1 | 10/1981 |
| DE | 3345067 A1 | 6/1984 |
| DE | 3537507 | 4/1987 |
| DE | 3539073 A1 | 5/1987 |
| DE | 4004157 C1 | 4/1991 |
| DE | 4343205 A1 | 6/1995 |
| DE | 197 35 359 | 1/1998 |
| DE | 297 23 101 | 7/1998 |
| DE | 298 10 846 | 8/1998 |
| DE | 298 10846 U1 | 8/1998 |
| EP | 0 054 154 | 10/1981 |
| EP | 0 252 052 A1 | 1/1988 |
| EP | 0 264 772 A1 | 4/1988 |
| EP | 0 386 605 A1 | 2/1990 |
| EP | 90427474 A2 | 5/1991 |
| EP | 0 462 701 | 12/1991 |
| EP | 0 462 701 A1 | 12/1991 |
| EP | 0 602 424 | 11/1993 |
| EP | 0 608 684 A1 | 8/1994 |
| EP | 0 0697 225 | 7/1995 |
| EP | 178 925 A2 | 4/1996 |
| EP | 0 747 078 A2 | 12/1996 |
| EP | 0 821 978 | 2/1998 |
| EP | 0 873 906 | 10/1998 |
| EP | 1 356 843 | 10/2003 |
| FR | 2 574 657 A1 | 6/1986 |
| FR | 2 658 725 A1 | 8/1991 |
| FR | 2 749 176 | 12/1997 |
| GB | 1395391 | 5/1975 |
| GB | 1 467 828 | 3/1977 |
| GB | 2145335 A | 3/1985 |
| GB | 2147506 A | 5/1985 |
| GB | 2 164 569 A | 3/1986 |
| GB | 2 186 801 | 8/1987 |
| GB | 2 267 648 A | 12/1993 |
| JP | 39-013991 | 7/1939 |
| JP | 52-076695 | 6/1977 |
| JP | 52-76695 | 12/1977 |
| JP | 6-184803 | 7/1994 |
| JP | 09/216240 A | 8/1997 |
| JP | 11-000397 | 1/1999 |
| JP | A-2000-135103 | 5/2000 |
| JP | 2000-515784 | 11/2000 |
| JP | 2003-502119 | 2/2003 |

(56) References Cited

FOREIGN PATENT DOCUMENTS

| JP | 2004-329941 | 11/2004 |
|---|---|---|
| JP | 3686609 | 8/2005 |
| WO | WO 82/03548 | 10/1952 |
| WO | WO 80/01044 | 5/1980 |
| WO | WO 86/06969 | 12/1986 |
| WO | WO 87/01950 | 4/1987 |
| WO | WO 90/01963 | 3/1990 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/39206 | 12/1996 |
| WO | WO 97/07847 | 3/1997 |
| WO | WO 97/41911 | 11/1997 |
| WO | WO 98/04310 | 3/1998 |
| WO | WO 98/11930 | 3/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/34665 | 8/1998 |
| WO | 98/48878 | 11/1998 |
| WO | WO 99/21618 | 5/1999 |
| WO | WO 00/57942 | 10/2000 |
| WO | WO 00/78384 | 12/2000 |
| WO | WO 02/07806 | 1/2002 |
| WO | WO 02/47749 | 6/2002 |
| WO | WO 2004/022144 | 3/2004 |
| WO | WO 2004/022145 | 3/2004 |
| WO | WO 2004/022146 | 3/2004 |
| WO | WO 2004/022147 | 3/2004 |

OTHER PUBLICATIONS

Office Action issued in a corresponding Japanese Application No. 2011-106504 (dated Nov. 13, 2012) with English translation thereof and Office Action Summary.
International Search Report for PCT/EP2004/012811 dated Apr. 12, 2005.
English Translation of Office Action from corresponding Chinese Patent Application No. 2004800402201.
English Translation of Japanese Office Action for Application No. 2001-504444, Mailed Oct. 26, 2004, 2 pages.
European Search Report dated Sep. 23, 2008, Appln. No. EP 08161868.8.
European Search Report issued in related EP Appln. 10185071 (mailed Dec. 6, 2010).
European Search Report issued in related EP Appln. 10185072 (mailed Dec. 6, 2010).
European Search Report issued in related EP Appln. 10185073 (mailed Dec. 6, 2010).
Japanese Office Action for Application No. 2005-004072, Mailed Sep. 24, 2009, including English translation.
Product Brochure for "Sullivan Miracle" Face Mask, ©1997, ResMed, 4 pages.
Product Brochure for "Sullivan Mirage" Face Mask, ©1998, ResMed, 4 pages.
Color Photo of "Weinmann Mask" 1998, 1 page.
"The ResMed Range of Mask Systems" product brochure, Nov. 1995, 4 pages.
"Somnotron CPAP-Gerat WM 2300" instruction manual, Weinmann Hamburg (1991), 11 pages.
9 photographs of Weinmann mask, WM 23122, 1991.
Mask 1 Photographs, Respironics Inc., Reusable Full Mask (small) Part #452033 Lot #951108.
Mask 2 Photographs, Puritan—Bennett, Adam Curcuit, Shell Part #231700, Swivel Part #616329-00, Pillows (medium) Part #616324.
Mask 3 Photographs, DeVilbiss Healthcare Inc., Devilbiss Seal-Ring and CPAP Mask Kit (medium), Part #73510-669.
Mask 4 Photographs, Respironics Inc., Monarch Mini Mask with Pressure Port. Part #572004, Monarch Headgear, Part #572011.
Mask 5 Photographs, Healthdyne Technologies, Nasal CPAP Mask (medium narrow), Part #702510.
Mask 6 Photographs, Healthdyne Technologies, Soft Series Nasal CPAP Mask, Part #702020.
Mask 7 Photographs, DeVilbiss Healthcare Inc., Small Mask and Seal Rings, Part #73510-668.
Mask 8 Photographs, Respironics Inc., Reusable Contour Mask (medium), Part #302180.
Mask 9 Photographs, Healthdyne Technologies, Healthdyne Large Headgear.
Mask 10 Photographs, Respironics Inc., Soft Cap (medium), Part #302142.
Mask 11 Photographs, Weinmann: Hamburg, Nasalmaskensystem mit Schalldämpfer (medium), Part #WN 23105.
Mask 12 Photographs, Life Care.
Mask 13 Photographs, Healthdyne Technologies.
Mask 14 Photographs, King System.
Mask 15 Photographs, Respironics Inc., Pediatric Mask.
Mask 16 Photo raphs, Hans Rudolph Inc.. Hans Rudolph Silicone Rubber Face Mask/8900.
Patent Examination Report No. 1 issued in a corresponding Australian Application No. 2012203522, dated Jul. 30, 2013.
Communication Pursuant to Article 94(3) EPC (Examination Report) mailed Sep. 18, 2015 in European Application No. 10 185 071.7 (6 pages).
Feb. 25, 2016 Minutes of the Oral Proceedings Before the Opposition Division issued in European Application No. 08161868.8 (5 pages).
Feb. 25, 2016 Decision Rejecting the Opposition (Article 101(2) EPC) issued in European Application No. 08161868.8 (5 pages).
Summons to Attend Oral Proceedings Pursuant to Rule 115(1) EPC mailed May 29, 2015 in European Patent No. 1985327 (EP Appln. No. 081611868.8) (7 pages).
Communication of a Notice of Opposition dated Jan. 22, 2014 issued in a corresponding EP Patent No. 1 985 327 (EP Appln. No. 08161868.8), together with a Notice of Opposition dated Jan. 13, 2014 (filed Jan. 15, 2014), together with an English translation (52 pages).

* cited by examiner

FIG. 16

FOREHEAD SUPPORT FOR FACIAL MASK

CROSS REFERENCE TO RELATED APPLICATIONS

This application is a continuation of U.S. application Ser. No. 12/585,732, filed Sep. 23, 2009, allowed, which is a divisional of U.S. application Ser. No. 11/510,607, filed Aug. 28, 2006, now U.S. Pat. No. 7,610,916, which is a continuation of U.S. application Ser. No. 10/700,252, filed Nov. 4, 2003, now U.S. Pat. No. 7,234,466, which is a continuation of U.S. application Ser. No. 10/264,326, filed Oct. 4, 2002, now U.S. Pat. No. 6,860,269, which is a continuation of U.S. application Ser. No. 09/502,745, filed Feb. 11, 2000, now U.S. Pat. No. 6,532,961, which claims the benefit of Australian Patent Application No. PQ 1040, filed Jun. 18, 1999, each incorporated herein by reference in its entirety.

FIELD OF THE INVENTION

The present invention relates to a forehead support for a facial mask used to supply breathable gas to a wearers airways.

The invention has been developed primarily for use in supporting a nasal mask used in Continuous Positive Airway Pressure (CPAP) treatment of, for example, Obstructive Sleep Apnea (OSA) and other ventilatory assistance treatments such as Non-Invasive Positive Pressure Ventilation (NIPPV) and will be described hereinafter with reference to this application. However, it will be appreciated that the invention is not limited to these particular uses and is also suitable for use with, for example, full-face (i.e. nose and mouth) masks.

BACKGROUND OF THE INVENTION

CPAP treatment is a common ameliorative treatment for breathing disorders including OSA. CPAP treatment, as described in U.S. Pat. No. 4,944,310, provides pressurised air or other breathable gas to the entrance of a patient's airways at a pressure elevated above atmospheric pressure, typically in the range 4-20 cm $H_2O$.

It is also known for the level of treatment pressure to vary during a period of treatment in accordance with patient need, that form of CPAP being known as automatically adjusting nasal CPAP treatment, as described in U.S. Pat. No. 5,245,995.

NIPPV is another form of treatment for breathing disorders which can involve a relatively higher pressure of gas being provided in the patient mask during the inspiratory phase of respiration and a relatively lower pressure or atmospheric pressure being provided in the patient mask during the expiratory phase of respiration.

In other NIPPV modes the pressure can be made to vary in a complex manner throughout the respiratory cycle. For example, the pressure at the mask during inspiration or expiration can be varied through the period of treatment, as disclosed in the applicant's international PCT patent application No. PCT/AU97/00631.

Typically, the ventilatory assistance for CPAP or NIPPV treatment is delivered to the patient by way of a nasal mask. Alternatively, a mouth mask or full face mask or nasal prongs can be used. In this specification any reference to a mask is to be understood as incorporating a reference to a nasal mask, mouth mask, full face mask or nasal prongs, unless otherwise specifically indicated.

In this specification any reference to CPAP treatment is to be understood as embracing all of the above described forms of ventilatory treatment or assistance.

A CPAP apparatus broadly comprises a flow generator constituted by a continuous source of air or other breathable gas such as a hospital piped supply or a blower. In the latter case, an electric motor drives the blower and is typically controlled by a servo-controller under the control of a microcontroller unit. In either case, the gas supply is connected to a conduit or tube which in turn is connected to a patient nasal or full-face mask which incorporates, or has in close proximity, an exhaust to atmosphere for venting exhaled gases. Examples of prior art nasal masks are shown in U.S. Pat. Nos. 4,782,832 and 5,243,971.

The supply conduit delivers gas into a chamber formed by walls of the mask. The mask includes a cushion positioned against the wearer's face and is normally secured to the wearer's head by straps. The straps are adjusted to pull the mask against the face to achieve a gas tight seal between the cushion and the wearer's face.

A problem that arises with existing masks is that with the use of straps, the mask is compressed against the wearer's face and may push unduly hard on the wearer's nose. Additionally, the mask may move around the wearer's face. Thus, there has been hitherto provided a forehead support, which provides a support mechanism between the mask and the forehead. This forehead support prevents both the mask from pushing too strongly against the wearer's nose and/or facial region as well as minimising movement of the mask with the addition of a contact point between the mask and the wearer's head thereby reducing uncomfortable pressure points. Additionally, the forehead support can be arranged to prevent the gas supply conduit from contacting the wearer's forehead or face.

Forehead supports with a single cushion and a single contact point on the forehead are known.

The applicant's U.S. patent application Ser. No. 09/008,708 relates to a substantially rigid one-piece forehead support having a pair of forehead cushions mounted at each outer end of the support. This forehead support is connected to the top of a facial mask and includes an adjustment mechanism to allow the spacing between the top of the facial mask and the forehead support to be altered between predetermined positions to alter the angle of the mask relative to the wearer's head to suit the wearer's facial topography.

The applicant's Australian provisional patent application No. PP9499 relates to a forehead support having a pair of pivotable arms that each have a forehead cushion mounted at their distal end. This forehead support is connected to the top of a mask and includes an adjustable mechanism to allow the angle between the arms to be altered between predetermined positions to alter the angle of the mask relative to the wearer's head to suit the wearer's facial topography.

It is an object of the present invention to provide an alternate form of forehead support.

SUMMARY OF THE INVENTION

Accordingly, in a first aspect, the present invention provides a forehead support adapted to be secured to a respiratory mask, said forehead support including a joining member for securing to the mask and a cushion frame pivotally mounted to the joining member, wherein: the cushion frame is adapted to locate one or more forehead cushions; the cushion frame is adapted to pivot relative to the joining member; and the cushion frame is selectively lockable at two or more predetermined angular positions relative to the joining member.

In a second aspect, the present invention provides a respiratory mask assembly comprising a respiratory mask and a forehead support adapted to be secured to the mask, said forehead support including a joining member for securing to the mask and a cushion frame pivotally mounted to the joining member, wherein: the cushion frame is adapted to locate one or more forehead cushions; the cushion frame is adapted to pivot relative to the joining member; and the cushion frame is selectively lockable at two or more predetermined angular positions relative to the joining member.

The cushion frame is preferably T-shaped and includes a forehead cushion at each end of the upper portion of the T.

Preferably, one of the cushion frame or joining member includes a tongue adapted to be received in one of at least two grooves provided on the other of the cushion frame or joining member so as to lock the cushion frame and joining member at one of the two or more predetermined angular positions.

More preferably, a pair of the tongues are provided on the cushion frame and at least two pairs of grooves are provided on the joining member.

The tongue(s) is/are preferably provided on a semi-rigid member which is adapted to permit the tongue(s) to be moved out of engagement with the grooves by manual manipulation of the member. The tongue(s) is/are preferably connected to a button adapted to protrude from the cushion frame to facilitate manual manipulation of the member.

The cushion frame preferably includes means to connect a head strap thereto.

The mask preferably also include means to connect a head strap thereto.

The joining member can be produced from, for example, polypropylene or polycarbonate.

The mask can include a mask shell and a mask cushion. The mask shell can be produced from, for example, polypropylene or polycarbonate.

The cushion frame can be produced from, for example, polypropylene or polycarbonate.

BRIEF DESCRIPTION OF THE DRAWINGS

Preferred embodiments of the invention will now be described, by way of examples only, with reference to the accompanying drawings in which.

DETAILED DESCRIPTION OF PREFERRED EMBODIMENTS

Figure 1:
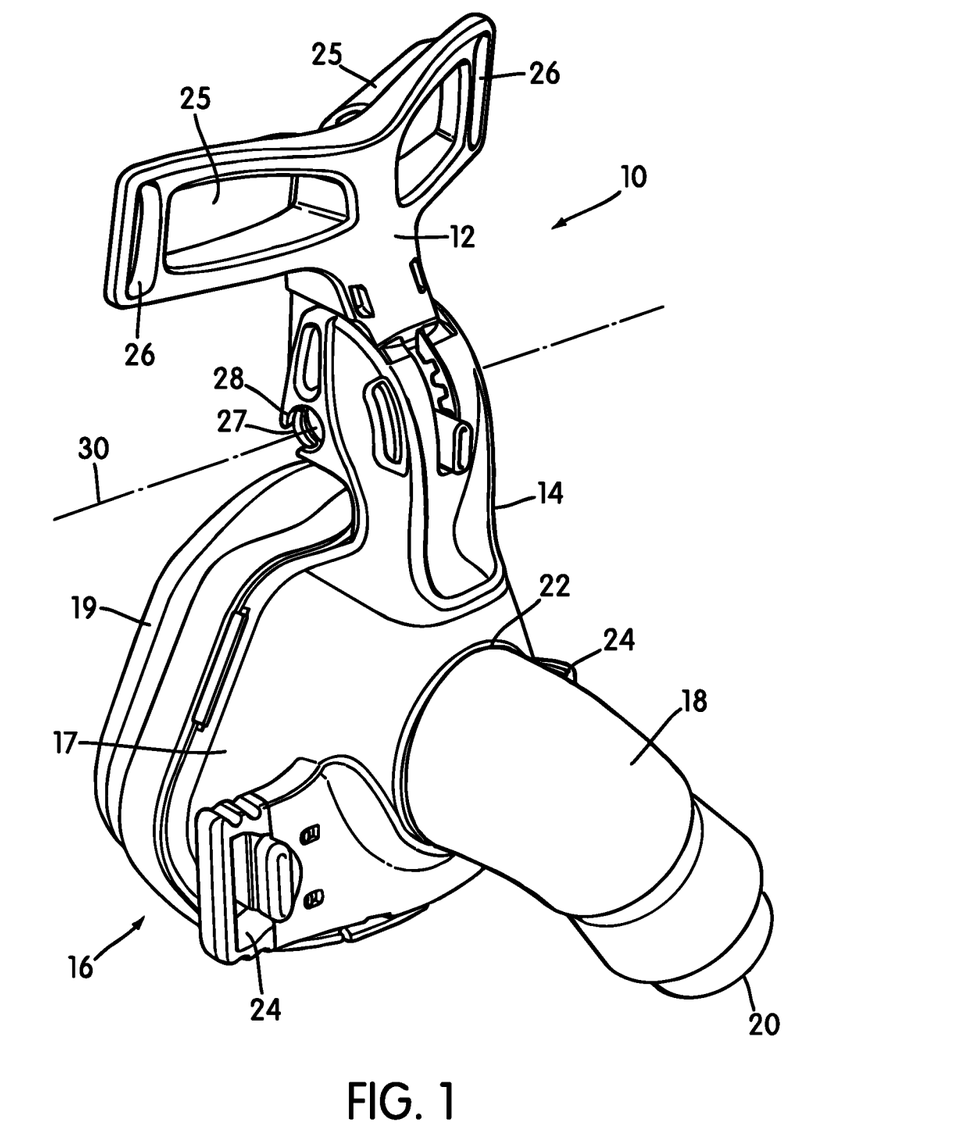
FIG. 1 is a front perspective view of a first embodiment of a forehead support according to the invention connected to a nasal mask.

FIG. 1 shows a first embodiment of a forehead support 10 according to the present invention. The forehead support 10 includes a generally T-shaped cushion frame 12 pivotally mounted to a joining member 14. The joining member 14 is connected to a nasal respiratory mask 16 used to supply breathable gas to a wearer's airways.

The mask 16 includes a mask shell 17 and a mask cushion 19. The mask shell 17 also includes an angled connector 18 which has a distal end 20 for connection to a gas supply conduit (not shown) and a proximal end 22 for connection to the mask 16. The connector 18 communicates the supplied gas from the gas supply conduit to the interior of the mask 16. The mask shell 17 also includes a pair of slotted connectors 24 to which are respectively connected ends of a lower head strap (not shown) for securing the nasal mask to the wearer's head.

The joining member 14 is connected on top of the mask shell 17 generally adjacent and above the wearer's nose. It will be appreciated that the nasal mask 16 shown is just one example of a respiratory mask that could be supported by the forehead support 10. For example, the forehead support also finds application in supporting full-face (i.e. nose and mouth) masks.

Forehead supports according to the invention can also be used with facial masks in which the gas supply connector 18 is incorporated into the mask in the general position of the joining member 14. In this type of mask, the supplied gas flows through or past the forehead support 10.

The T-shaped cushion frame 12 includes a pair of forehead cushions 25 mounted at each end of the upper portion of the T on the wearer contacting side. Examples of cushions 25 include open or closed cell foam, silicone, dual durometer foams, single pads or multiple pads joined together. The forehead cushions 25 can be integrally moulded with the frame 12 or attached thereto by clips or adhesives or the like. The frame 12 also includes a slotted connector 26 adjacent each of the forehead cushions 25 to which are respectively connected ends of an upper head strap (not shown) for securing the cushion frame 12 to the wearer's head.

The T-shaped cushion frame 12 also includes a pair of shafts 27 (only one shown) on the lower portion of the T which are each respectively received in part circular openings 28 (only one shown) provided on the joining member 14. The shafts 27 can pivot or rotate in their respective openings 28 to provide for pivotal or rotational movement between the cushion frame 12 and the joining member 14 about axis 30 in the direction of double-headed arrow 31.

The curved shape of the cushions 25 allows them to effectively "roll" over the wearer's forehead during angular adjustment between the cushion frame 12 and the joining member 14.

Figure 2:
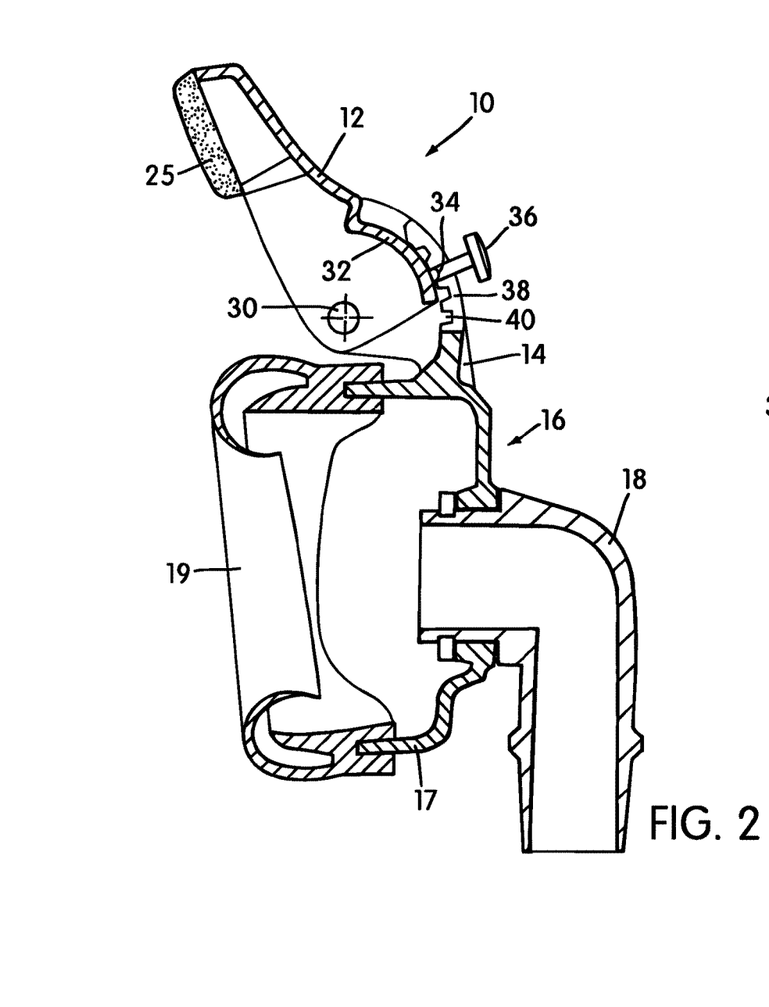
FIG. 2 is a cross sectional side view of the forehead support shown in FIG. 1 with the tongue of the cushion frame engaged with one of the pairs of grooves of the joining member.
Figure 3:
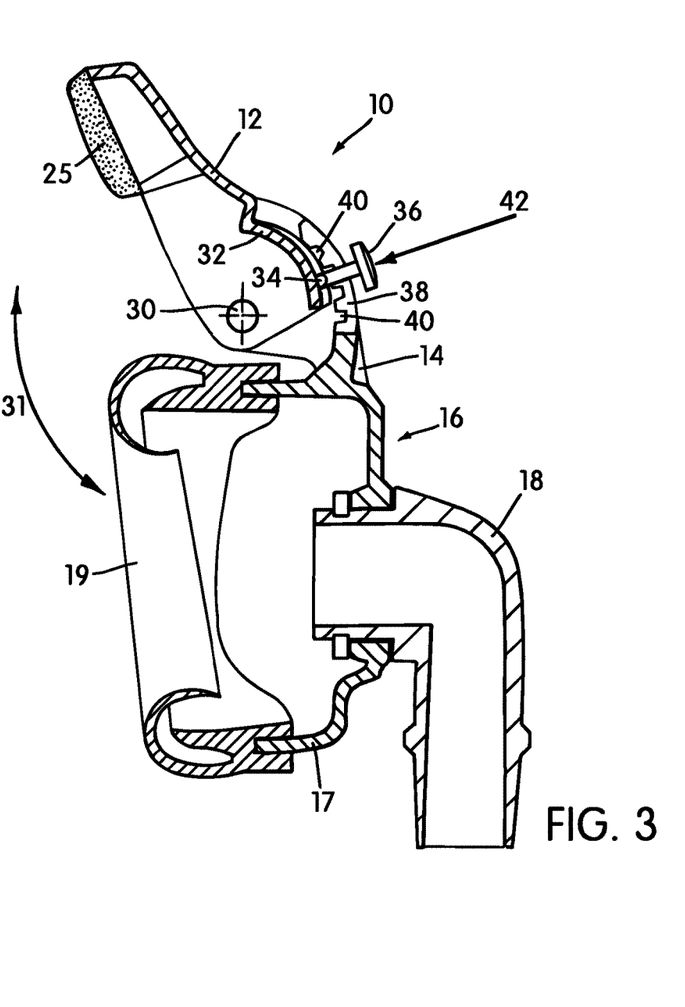
FIG. 3 is a cross sectional side view of the forehead support shown in FIG. 1 with the tongue of the cushion frame free of engagement with the pairs of grooves of the joining member.
Figure 4:
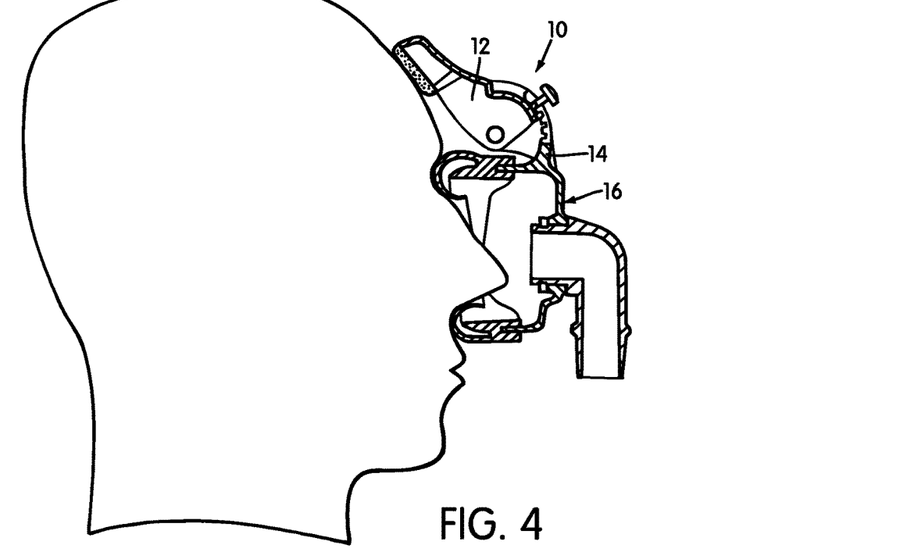
FIG. 4 is a cross sectional side view of the forehead support shown in FIG. 1 adjacent a wearer's head with the tongues and grooves engaged at the first of four positions.
Figure 5:
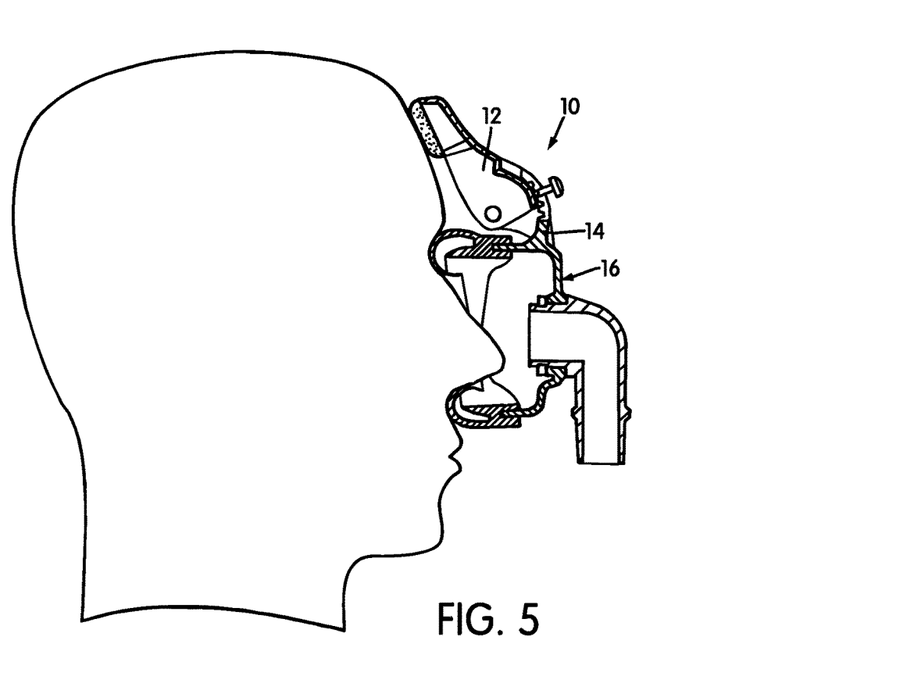
FIG. 5 is a cross sectional side view of the forehead support shown in FIG. 1 adjacent a wearer's head with the tongues and grooves engaged in the second of four positions.

As best shown in FIGS. 2 and 3, the cushion frame 12 also includes a flexible member 32 which has two side by side spaced apart tongues 34 and a middle protruding button 36 on its distal end. The joining member 14 also includes two generally arcuate shaped portions 38 that each have a pair of four grooves 40. It will be appreciated that the pair of four grooves is merely preferable and that only two or more grooves are required. It will also be appreciated that the flexible member 32 can be on the joining member 14 and the grooves 40 can be on the cushion frame 12. The tongue 34 and the grooves 40 extend in a direction substantially parallel to a line extending radially from the axis 30.

The cushion frame 12 is constructed from a plastics material, such as polypropylene or polycarbonate, which allows the member 32 to be flexed relative to the cushion frame 12 upon which is mounted when pressure is applied to the button 36 in the direction of arrow 42. The corresponding movement of the tongues 34 releases them from engagement with one of the pairs of grooves 40 (as shown in FIG. 3) to allow angular adjustment between the cushion frame 12 and the joining member 14 about the axis 30. Releasing the button 36 allows the tongue 34 to resiliently flex back towards the grooves 40. When the tongues 34 and one of the pairs of grooves 40 are aligned (as shown in FIGS. 2 and 4 to 7) the tongues 34 engage one of the pair of grooves 40. When the tongues 34 are engaged with one of the pair of grooves, the cushion frame 12 and joining member 14 are locked against pivotal movement therebetween at a predetermined angle.

FIGS. 4 to 7 respectively show forehead support 10 adjacent the heads of different wearers with the tongues 34 engaged in the first, second, third and fourth of the four pairs of grooves 40.

Figure 6:
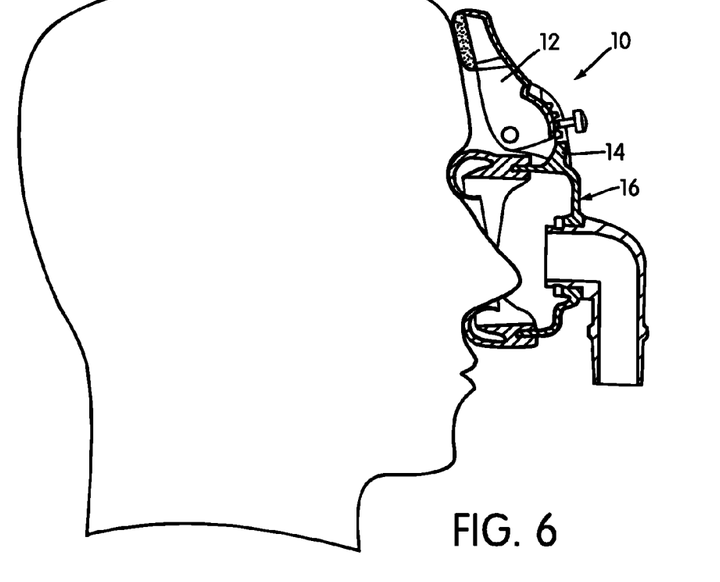
FIG. 6 is a cross sectional side view of the forehead support shown in FIG. 1 adjacent a wearer's head with the tongues and grooves engaged at the third of four positions.
Figure 7:
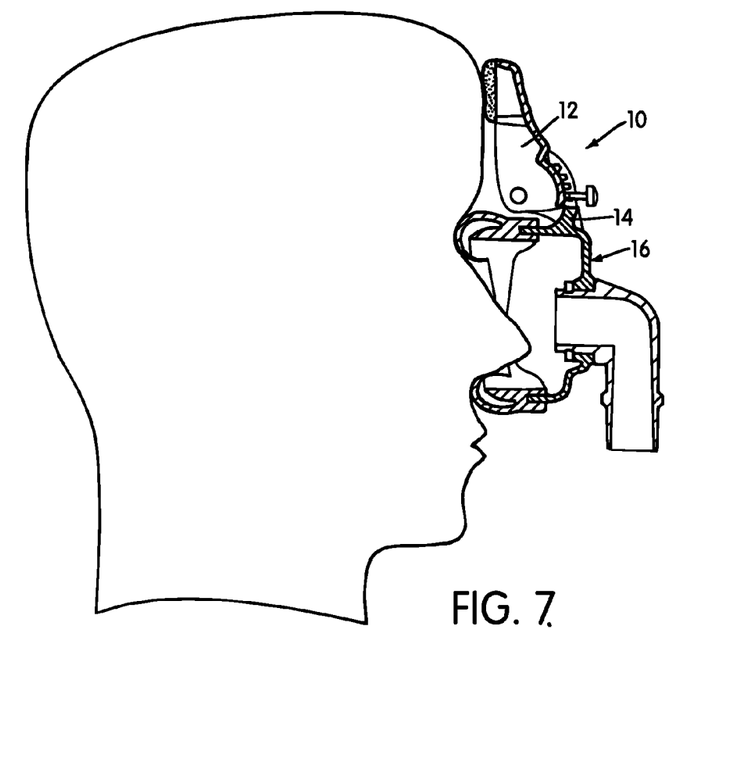
FIG. 7 is a cross sectional side view of the forehead support shown in FIG. 1 adjacent a wearer's head with the tongues and grooves engaged at the fourth of four positions.

As FIGS. 4 to 7 show, the angle between the cushion frame 12 and the joining member 14 adjacent the wearer's forehead can be increased to suit wearer's with relatively high nasal regions and relatively low foreheads (FIGS. 4 and 5) and decreased to suit wearers with relatively low nasal regions and relatively high foreheads (FIGS. 6 and 7).

In this way the forehead support 10 advantageously allows the mask 16 to be positioned to comfortably suit the particular topography of the wearer's face to ensure the mask cushion 19 is positioned ideally relative to the wearer's face. As examples, the relative position of the cushion frame 12 and the joining member 14 in FIG. 4 would be more suitable for use with a wearer having a shallow forehead or protruding cheeks or nose whilst the position of the cushion frame and joining member 14 in FIG. 7 would be more suitable for use with a wearers having a protruding or bulbous forehead.

Figure 8:
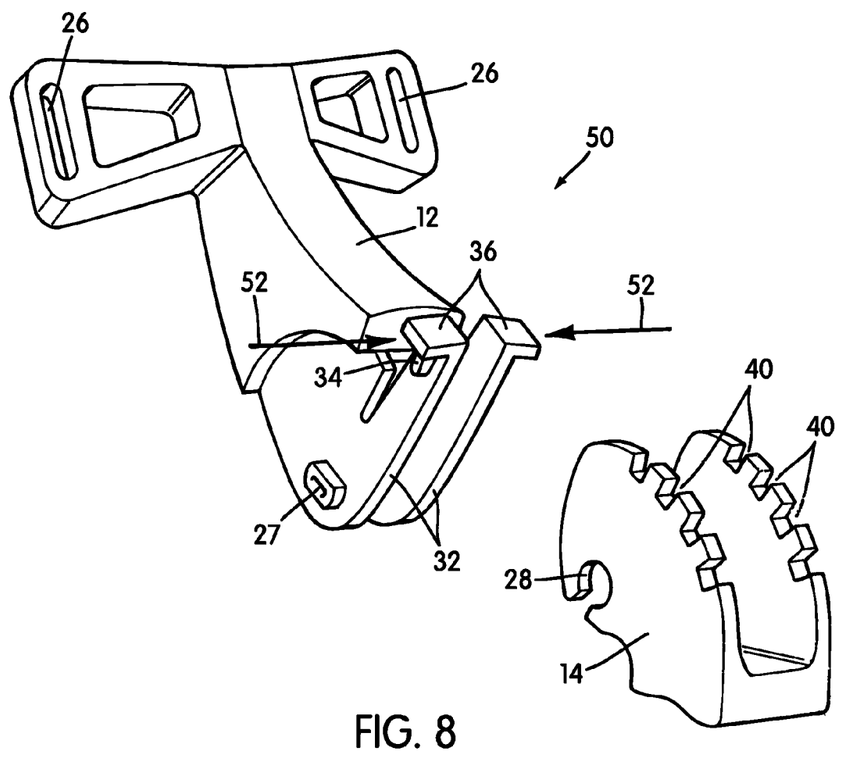
FIG. 8 is a partial exploded perspective view of a second embodiment of a forehead support according to the invention.

FIG. 8 shows a second embodiment of a forehead support 50 according to the present invention Like reference numerals to those used in describing the first embodiment will be used to denote like features in relation to the second embodiment.

In the second embodiment, their are two buttons 36. Pressing the buttons together in the direction of arrows 52 flexes the tongues 34 towards each other to disengage them from the grooves 40 and allow angular adjustment between the cushion frame 12 and the joining member 14. Releasing the buttons 36 allows the tongues 34 to resiliently flex towards, and into engagement with, the grooves 40 to lock the cushion frame 12 and the joining member 14 against relative pivotal movement.

FIGS. 9 to 14 show a third embodiment of a forehead support 60 according to the present invention. Like reference to those used in describing the first embodiment will also be used to denote like features in relation to the third embodiment.

Figure 9:
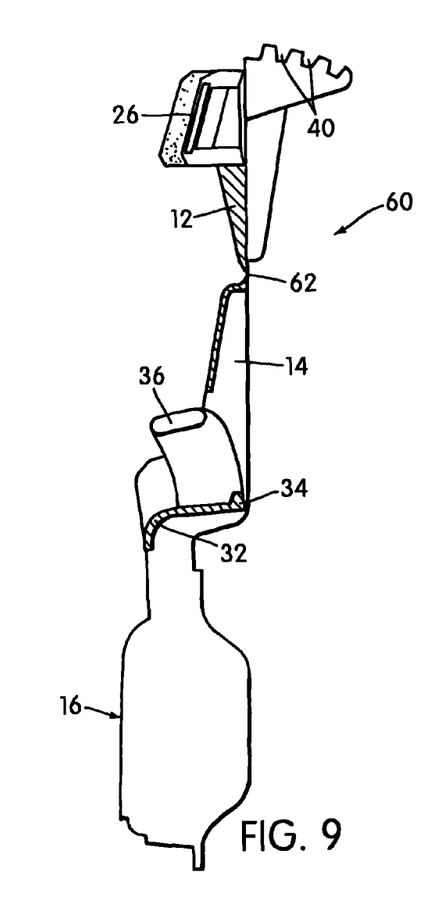
FIG. 9 is a cross sectional side view of a third embodiment of a forehead support according to the invention that includes an integrally formed cushion frame and joining member.
Figure 10:
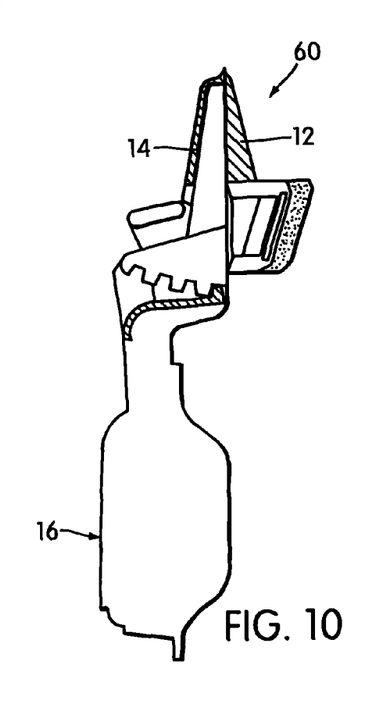
FIG. 10 is a cross sectional view of the forehead support shown in FIG. 9 with the tongue and grooves engaged at the first of four positions.
Figure 11:
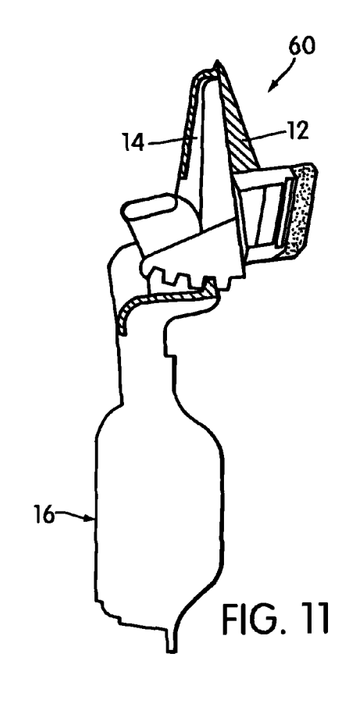
FIG. 11 is a cross sectional view of the forehead support shown in FIG. 9 with the tongue and grooves engaged at the second of four positions.
Figure 12:
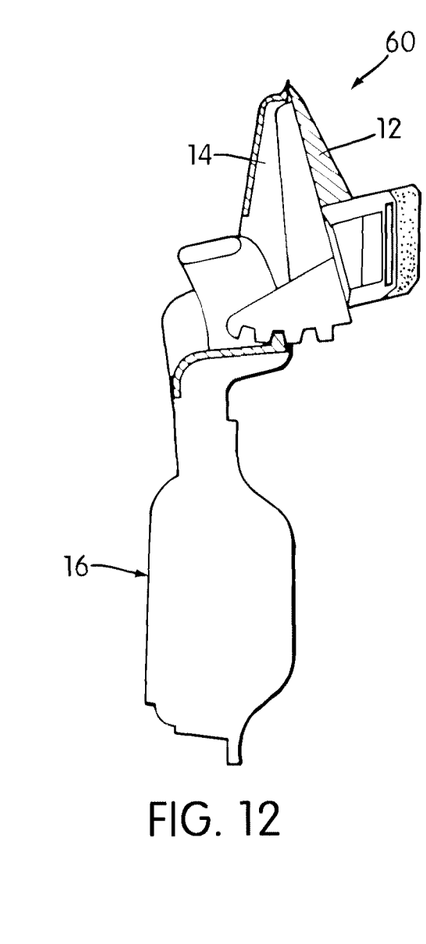
FIG. 12 is a cross sectional view of the forehead support shown in FIG. 9 with the tongue and grooves engaged at the third of four positions.
Figure 13:
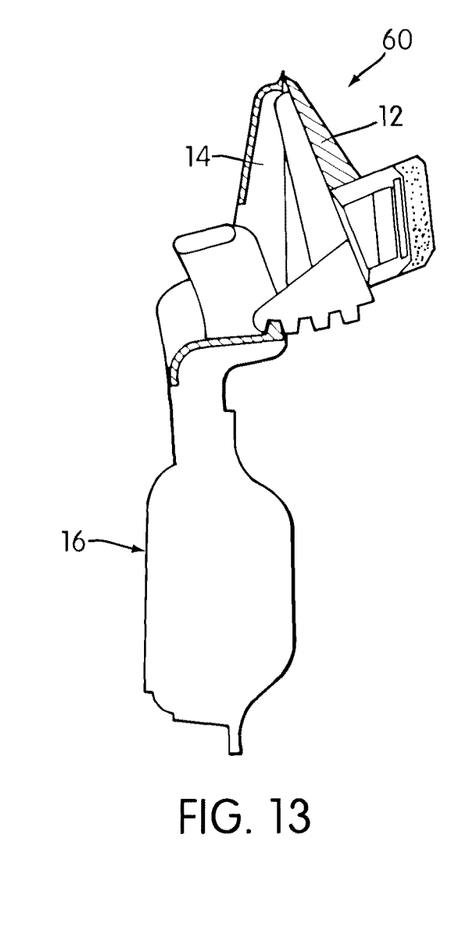
FIG. 13 is a cross sectional view of the forehead support shown in FIG. 9 with the tongue and grooves engaged at the fourth of four positions.
Figure 14:
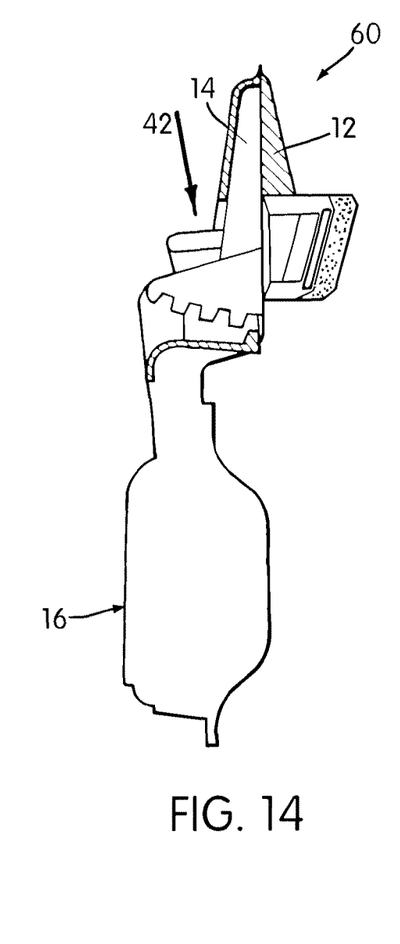
FIG. 14 is a cross sectional view of the forehead support shown in FIG. 9 with the tongue free of engagement with the grooves.

In the third embodiment, the cushion frame 12 is integrally moulded with the joining member 14 and joined by an integral hinge 62 (sometimes known as a natural or living hinge). The cushion frame 12 and the joining member 14 can be pivoted relative to each other about the hinge 62. The forehead support 60 is moulded in a substantially 'flat' configuration, as shown in FIG. 9. The cushion frame 12 is then pivotted through approximately 180° relative to the joining member 14 until the tongue 34 engages one of the four grooves 40. As with the earlier embodiments, pressing the button 36 in the direction of arrow 42 frees the tongue 34 from engagement with the grooves to allow adjustment of the angle between the cushion frame 12 and the joining member 14. The button 36 and the tongue 34 are inherently biased to a position engaging one of the grooves 40, again consistent with earlier embodiments.

In the preferred form shown, the mask shell 17 is also integrally formed with the joining member 14. This simplifies manufacturing and assembly and reduces production costs. The forehead support 60 is preferably manufactured from polypropylene due to its ability to mould integral hinges.

Figure 15:
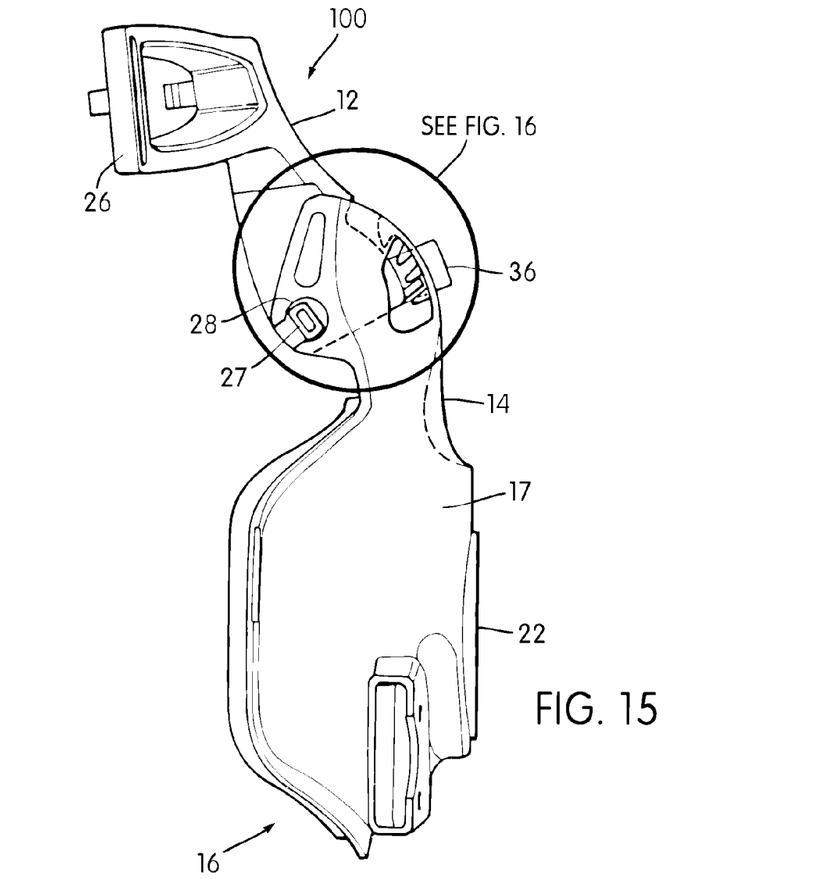
FIG. 15 is a side view of a fourth embodiment of a forehead support according to the invention.
Figure 16:
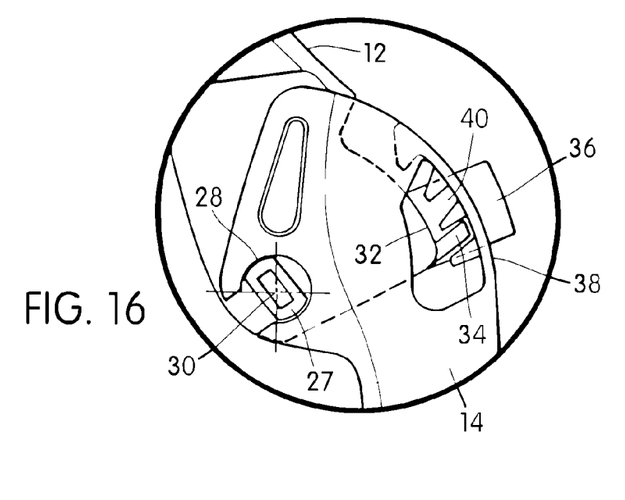
FIG. 16 is an enlarged side view showing enlarged details of a portion of the forehead support shown in FIG. 15.

FIGS. 15 and 16 show a fourth embodiment of a forehead support 100 according to the invention. Like reference to those used in describing the first embodiment will also be used to denote like features in relation to the fourth embodiment.

The fourth embodiment is almost identical to the first embodiment except the tongue 34 and the grooves 40 are angled with respect to a line extending radially from the axis 30 to the tongue 34 or the grooves 40. This angled arrangement reduces the likelihood that the tongue 34 will inadvertently release from engagement with one of the grooves 40 if the front of the mask 16 is subjected to a force in the direction of the wearer's face.

Although the invention has been described with reference to a specific example, it will be appreciated by those skilled in the art that the invention may be embodied in many other forms.

As an example, the forehead support can include means to resiliently bias the cushion frame and the joining member relative to one another such that they increase or decrease their angle relative to one another when the tongues are disengaged from one of the pairs of slots.

We claim:
1. A respiratory mask assembly comprising:
   a respiratory mask including a mask shell and a mask cushion;

a forehead support adjustably coupled to the mask, the forehead support including a joining member provided to the mask shell and a cushion frame pivotally mounted to the joining member so that the cushion frame can change an angular position with respect to the mask shell, wherein the cushion frame is adapted to be selectively locked against pivotal movement relative to the joining member in at least three predetermined angular positions by a tongue and slot arrangement including a tongue adapted to be received in one of at least three slots so as to lock the cushion frame and joining member at one of the at least three predetermined angular positions; and an angular adjustment member to allow selection between the at least three predetermined angular positions, the angular adjustment member including a pair of flexible arms spaced from one another a predetermined distance, the flexible arms are adapted to be flexed in a flexed configuration such that they flex toward one another to disengage the tongue from a respective one of the at least three slots, and the flexible arms are adapted to be released from the flexed configuration to allow the flexible arms to resiliently flex away from one another to engage the tongue in the respective one of the least three slots.

2. A respiratory mask assembly according to claim 1, wherein each flexible arm of the pair of flexible arms includes an angled end portion adapted for manual manipulation, the angled end portions extending in directions opposite one another.

3. A respiratory mask assembly according to claim 1, wherein the forehead support pivots relative to the mask about a generally fixed pivot axis.

4. A respiratory mask assembly according to claim 3, wherein the pair of flexible arms extend substantially perpendicular to the pivot axis.

5. A respiratory mask assembly according to claim 1, wherein the cushion frame is adapted to locate one or more forehead cushions.

6. A respiratory mask assembly according to claim 1, wherein the cushion frame include an upper cross portion that supports a forehead cushion and extends substantially parallel to an axis about which the cushion frame pivots.

7. A respiratory mask assembly according to claim 1, wherein the cushion frame and joining member include at least one shaft and slot assembly by which the cushion frame pivots.

8. A respiratory mask assembly according to claim 1, wherein the cushion frame includes a slotted head strap connector portion at each lateral end of the cushion frame.

9. A respiratory mask assembly according to claim 1, wherein the mask includes a swivel elbow through which pressurized breathable gas is supplied.

10. A respiratory mask assembly according to claim 1, wherein the mask is a nasal mask.

11. A respiratory mask assembly according to claim 1, wherein the mask is a full-face mask.

12. A respiratory mask assembly according to claim 1, wherein the angular adjustment member is centrally located on a lower end of an upright portion of the cushion frame.

13. A respiratory mask assembly according to claim 1, wherein the angular adjustment member is oriented towards a front and top of the mask shell.

14. A respiratory mask assembly according to claim 1, wherein the angular adjustment member provides one-handed operation to symmetrically adjust the position of the cushion frame.

15. A respiratory mask assembly to supply breathable gas to a wearer's airways, comprising:
a mask shell;
a mask cushion provided to the mask shell;
a forehead support including a forehead cushion frame and a joining member integrally moulded with the forehead cushion frame and joined by an integral hinge such that the forehead cushion frame and the joining member are pivotable relative to each other about the integral hinge; and
a locking mechanism to selectively lock the forehead cushion frame in two or more predetermined angular positions relative to the joining member.

16. The respiratory mask assembly according to claim 15, wherein the mask shell is integrally formed with the joining member.

17. The respiratory mask assembly according to claim 15, wherein the forehead support is moulded from polypropylene.

18. The respiratory mask assembly according to claim 15, wherein the locking mechanism comprises a tongue and groove arrangement.

19. The respiratory mask assembly according to claim 18, wherein the locking mechanism includes an adjustment member to engage and disengage the tongue and groove arrangement.

20. The respiratory mask assembly according to claim 19, wherein the adjustment member includes a flexible member and button protruding from the flexible member, and the flexible member includes a tongue adapted to be received in at least one groove.

21. The respiratory mask assembly according to claim 20, wherein the button and the tongue are inherently biased to a position engaging said at least one groove.

22. The respiratory mask assembly according to claim 15, wherein the forehead cushion frame is adapted to locate one or more forehead cushions.

23. The respiratory mask assembly according to claim 15, wherein the forehead cushion frame includes a slotted head strap connector adapted to connect a head strap.

24. The respiratory mask assembly according to claim 15, wherein the integral hinge is a living hinge.

25. A method of manufacturing a respiratory mask assembly comprising:
moulding a forehead support including a forehead cushion frame and a joining member in a substantially flat configuration;
pivoting the forehead cushion frame through approximately 180 degrees relative to the joining member; and
engaging a locking mechanism to selectively lock the forehead cushion frame in a predetermined angular position relative to the joining member.

26. The method according to claim 25, wherein moulding a forehead support includes joining the forehead cushion frame to the joining member by an integral hinge such that the forehead cushion frame and the joining member are pivotable relative to each other about the integral hinge.

27. The method according to claim 25, further comprising integrally molding a mask shell with the joining member.

28. The method according to claim 25, wherein moulding a forehead support includes molding the forehead support from polypropylene.

29. The method according to claim 25, wherein engaging a locking mechanism includes engaging a tongue in one of at least two grooves.

30. The method according to claim 25, wherein the joining member and the forehead support are formed in one piece and connected via a living hinge.

* * * * *